United States Patent [19]
Cresson et al.

[11] Patent Number: 5,138,878
[45] Date of Patent: Aug. 18, 1992

[54] FIBER ORIENTATION SENSOR

[75] Inventors: Thierry M. Cresson, Cupertino; Lee M. Chase, Los Gatos; Leonard M. Anderson; John D. Goss, both of San Jose, all of Calif.

[73] Assignee: Measurex Corporation, Cupertino, Calif.

[21] Appl. No.: 635,291

[22] Filed: Dec. 28, 1990

[51] Int. Cl.⁵ .......................... G01L 5/04; G01L 5/10; G01N 33/36; G01N 3/20
[52] U.S. Cl. .......................................... 73/159; 73/852
[58] Field of Search .......................... 73/159, 852, 849; 162/49, 263

[56] References Cited

U.S. PATENT DOCUMENTS

| | | | |
|---|---|---|---|
| 2,834,203 | 5/1958 | Sampson | 73/81 |
| 3,158,021 | 11/1964 | Walters et al. | 73/159 |
| 3,204,454 | 9/1965 | Friman et al. | 73/862.04 |
| 3,677,076 | 7/1972 | Herzhoff et al. | 73/159 |
| 4,581,575 | 4/1986 | Osaki et al. | 73/159 |
| 4,864,851 | 9/1989 | Haughton | 73/159 |
| 4,866,984 | 9/1989 | Houghton | 73/159 |
| 4,936,140 | 6/1990 | Houghton et al. | 73/159 |
| 4,936,141 | 6/1990 | Anderson, Jr. et al. | 73/159 |
| 4,970,895 | 11/1990 | Houghton et al. | 73/159 |
| 4,991,432 | 2/1991 | Houghton et al. | 73/159 |
| 5,010,766 | 4/1991 | Typpo | 73/159 |

FOREIGN PATENT DOCUMENTS 0934328 8/1963 United Kingdom ............... 73/159

OTHER PUBLICATIONS

Dahl, H. et al., "The Influence of Headbox Flow Conditions on Paper Properties and their Constancy", Tappi Journal, pp. 93-98 (Feb. 1988).

Primary Examiner—William A. Cuchlinski, Jr.
Assistant Examiner—Diego F. F. Gutierrez
Attorney, Agent, or Firm—Spensley Horn Jubas & Lubitz

[57] ABSTRACT

A sensor for detecting directional variations in a physical characteristic of a moving sheet of material is disclosed. The sensor has a support for supporting the moving sheet. The support defines an open region into which the moving sheet is deflected by a deflector. Detectors coupled to the support detect and produce signals indicative of the force exerted on the support by the deflected sheet in at least three different directions. Each signal is processed to determine a physical characteristic, such as extensional stiffness, of the sheet of material in each of the three directions. The directional variations of the physical characteristic may be used to determine the fiber orientation angle and the degree of anisotropism of the sheet.

19 Claims, 3 Drawing Sheets

FIBER ORIENTATION SENSOR

BACKGROUND OF THE INVENTION

1. Field of the Invention

The present invention relates to a sensor for determining directional variations in a physical characteristic in a moving sheet of material. In particular, the present invention relates to a sensor for determining the orientation of fibers in a moving sheet of fibrous material based upon the directional variation of a physical characteristic, and a method of using the sensor.

2. Description of Related Art

Many of the qualities and characteristics of a fibrous sheet material depend, at least in part, on the orientation of the fibers forming the material. Furthermore, the orientation of the fibers within the sheet material can, to a certain degree, be controlled during the manufacturing process.

For example, paper is typically formed by ejecting a slurry of water and paper pulp fibers from a headbox onto a moving porous belt, frequently called a "wire." The water component of the slurry drips through the wire leaving a mat of paper fibers on the wire. The mat is then subject to additional processing, such as pressing, drying, calendering, coloring, coating or the like to form a finished paper product. Many of the qualities and characteristics of the finished paper product are related to the orientation of the paper pulp fibers in the original mat.

That is, as the slurry is ejected onto the moving wire the paper pulp fibers may have a tendency or probability to become longitudinally oriented in one particular direction. If this tendency is high, a large number of fibers are oriented in one particular direction and the resulting paper product will be highly anisotropic. If the probability or tendency of the fibers to be oriented in any particular direction is low, that is the fibers are truly in a random orientation, the resulting paper product will be isotropic. The properties, such as tensile strength, of anisotropic products may exhibit directional variations while the properties of isotropic products tend to be independent of direction. Depending on the intended application, the optimum degree of anisotropism may vary.

Furthermore, for anisotropic products, the direction of predominant fiber orientation is also important. The directionality of the properties of anisotropic products usually depends on the predominant direction of fiber orientation. That is, if the predominant fiber orientation is at an angle to the machine direction, then the directionally dependant properties will typically exhibit either a maximum or a minimum at the same angle. Therefore, information relating to both the direction of the predominant fiber orientation, or the fiber orientation angle, as well as the degree of anisotropism is useful in evaluating fiber orientation in a fibrous sheet of material. Typically, in papermaking, the fiber orientation angle is defined as the angle between the machine direction, the direction of the moving wire, and the predominant direction of fiber orientation.

The tendency of the paper pulp fibers to have particular orientation depends on a large number of factors, including the geometry of the headbox, the speed of the wire, the speed of the ejected slurry, the direction of the ejection of the slurry relative to the wire, and cross-currents within the slurry. Many of these factors can be controlled. Therefore, it is useful to be able to quickly and accurately measure the degree of anisotropism and the fiber orientation angle during the manufacturing process. This allows for the manufacturing process to be adjusted to achieve the desired product qualities.

One present method of determining fiber orientation involves, measuring and counting the orientation of individuals fibers within the fibrous sheet. Because this method is extremely labor intensive, it is expensive, time consuming, and generally impractical for use in a manufacturing situation.

Another, presently used method of measuring the fiber orientation in a fiber sheet utilizes the relationship between tensile strength and fiber orientation. In this method, the tensile strength of a sample of the fibrous sheet is tested in several directions. A polar plot of the measured tensile strengths typically results in a shape resembling an ellipse. The ratio of the major axis of the ellipse to the minor axis of the ellipse provides an indication of the degree of anisotropism of the fibers in the sheet. Further, the angle between the major axis of the ellipse and the machine direction corresponds to the fiber orientation angle.

Although this test has been found to be relatively reliable, it is destructive to the fibrous sheet, time consuming, and cannot be conducted on-line. Given the speed of modern paper making equipment, this can result in the production of large quantities of substandard product before the test results are available. Furthermore, because the fiber orientation can vary substantially in the cross direction, i.e., across the width of the wire normal to the machine direction, the test must be conducted on samples taken at various intervals, or slices, across the sheet. This further increases the time and expense of this method of determining fiber orientation.

In addition, a number of devices employing optical, sonic, X-ray, or microwave attenuation techniques have been devised to measure fiber orientation. However, such devices are typically expensive, and are not well suited for the harsh environment often found in paper mills.

SUMMARY OF THE INVENTION

Accordingly, it is an object of the present invention to provide a sensor which can provide information about the directional variation of a physical characteristic of a moving sheet of material.

Another object of the invention is to provide a sensor that is reliable and well suited for use on-line in a manufacturing environment.

Yet another object of the invention is to provide a sensor that is relatively inexpensive and easy to install, use, and maintain.

In accordance with these and other objects, a sensor in accordance with one embodiment of the present invention includes a support for supporting the moving sheet of material. The support defines an open region into which the moving sheet is deflected by a deflector. Detectors coupled to the support detect and produce signals indicative of the force exerted on the support by the deflected sheet in at least three different directions. Each signal is processed to determine a physical characteristic of the sheet of material in each of the three directions.

In another aspect of the invention the sheet is a fibrous material and the signals are processed to determine a physical characteristic, such as extensional stiffness, which is related to the orientation of the fibers within the material. Information, such as the fiber orientation angle or the degree of anisotropism, can then be determined from the directional variations of the physical characteristic.

Other objects and aspects of the invention will become apparent to those skilled in the art from the detailed description of the invention which is presented by way of example and not as a limitation of the present invention.

DESCRIPTION OF E ILLUSTRATED EMBODIMENT

Figure 1:
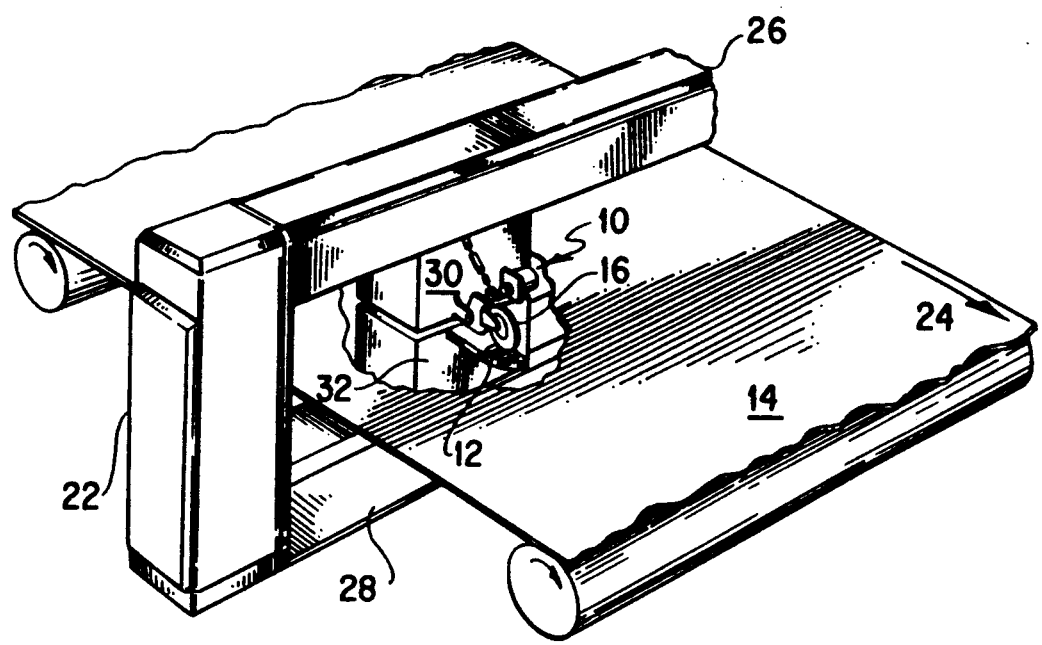
FIG. 1 illustrates a scanner having a preferred embodiment of the present sensor mounted thereto for scanning the sensor repeatedly across the width of the sheet of moving material.

A sensor in accordance with a preferred embodiment of the present invention is indicated as reference numeral 10 in FIG. 1. The illustrated sensor 10 has a sheet support ring 12 positioned on one side of a moving sheet of material 14; paper in the illustrated embodiment. A rotating wheel 16 is positioned on the other side of the moving sheet 14 to deflect the sheet into the opening defined by the ring 12. A number of segments 18a-18l are distributed about the inner periphery of the ring 12. Associated with each segment 18a-18l is a load cell 20a-20l, respectively, which can be used to measure the force exerted by the deflected sheet 14 on each segment 18a-18l. In this manner, the sensor 10 can detect the force exerted by the sheet 14 in the direction of each segment 18a-18l.

In the illustrated embodiment, the sensor 10 is carried by a scanning station 22 which scans the sensor 10 back and forth across the width of the sheet 14 which is moving in the direction of arrow 24. In this manner the sensor 10 can take readings at predetermined intervals, or slices, across the width of the sheet 14 and detect any variations in the measured physical characteristic in the cross direction.

The scanning station 22 can be one of many types well known to those skilled in the art. The illustrated scanning station 22 includes two beams 26 and 28 which extend transversely across the width of the moving sheet 14. One beam 26 is positioned above the moving sheet 14 and the other beam 28 is positioned below the moving sheet. Upper and lower gauge support members are mounted to the upper and lower beams 26 and 28, respectively. In the illustrated embodiment, the upper gauge support member 23 carries the wheel 16 and the lower gauge support member 32 carries the ring 12. The two gauge support members 30 and 32 are positioned in vertical alignment with respect to each other position the wheel 16 within the opening defined by the ring 12. In FIG. 1, a portion of the sheet is cut away showing the relationship between the upper and lower gauge support members 30 and 32, respectively. A motor (not shown) within the scanning system drives the gauge support members 30 and 32 back and forth across the moving sheet 14 in a continuous scanning motion. The movement of the upper and lower gauge support members 30 and 32 is synchronized to maintain a constant vertical alignment between the wheel 16 and the opening defined by the ring 12 at all times during the scanning motion.

Figure 2:
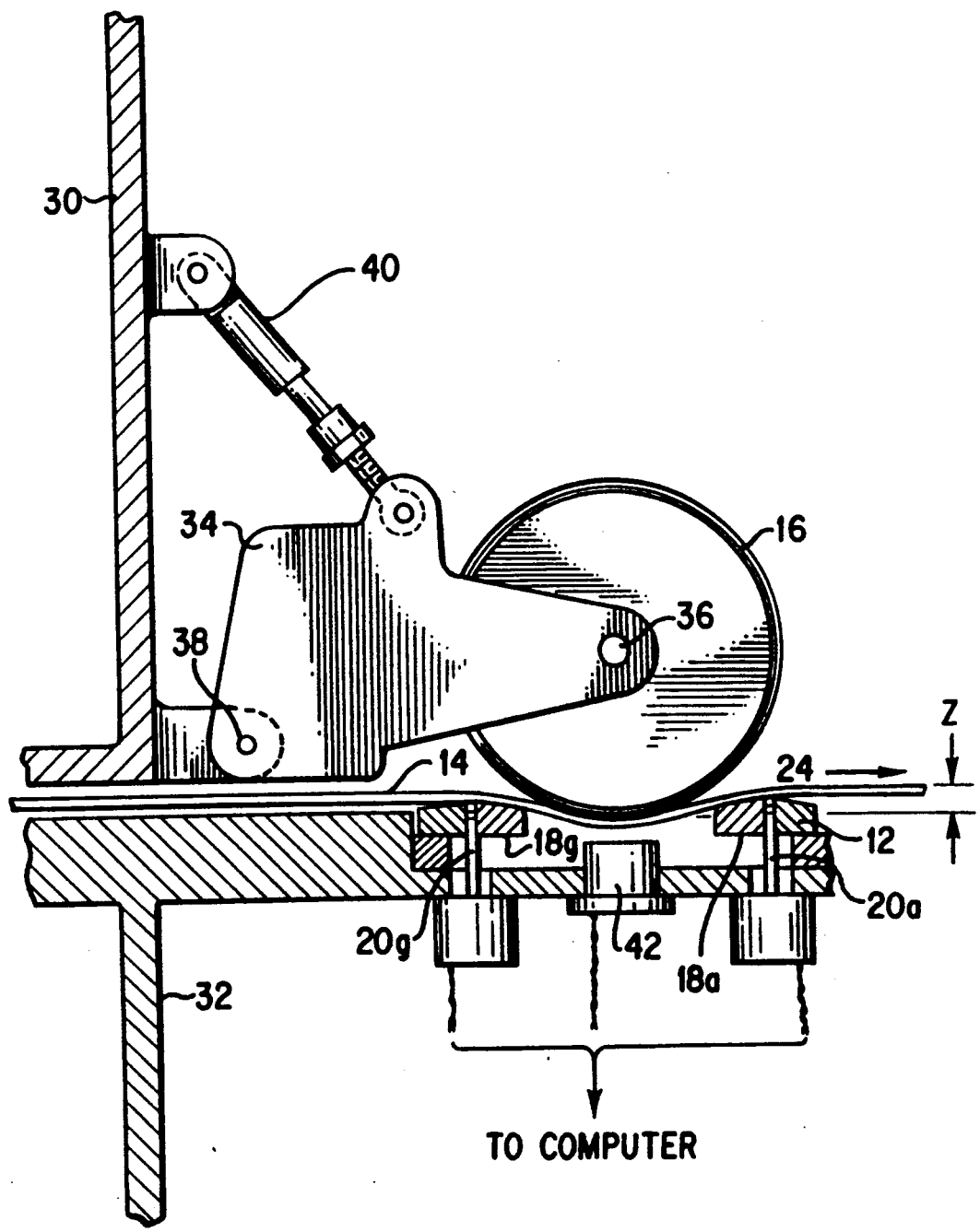
FIG. 2 is a partially cut away side view of the sensor shown in FIG. 1.

As best seen in FIG. 2, the wheel 16 is mounted to wheel carrier 34 for rotation about a central axle 36. The wheel carrier 34 is pivotally mounted to the upper gauge support member 30 by pivot pin 38. An adjustable air cylinder 40 with one end fastened to the upper support member 30 and the other end fastened to the wheel carrier can be extended or retracted to vary the distance, z, which the wheel 16 deflects the moving sheet 14. Preferably, a computer (not shown) is operatively coupled to the air cylinder 40 to control the deflection distance. Preferably, the periphery of the wheel 16 is spherically convex rather than cylindrical, such that the sheet is deflected uniformly in all directions and the deflection is generally symmetrical in all directions about the lowest point of the rotating wheel 16.

Figure 3:
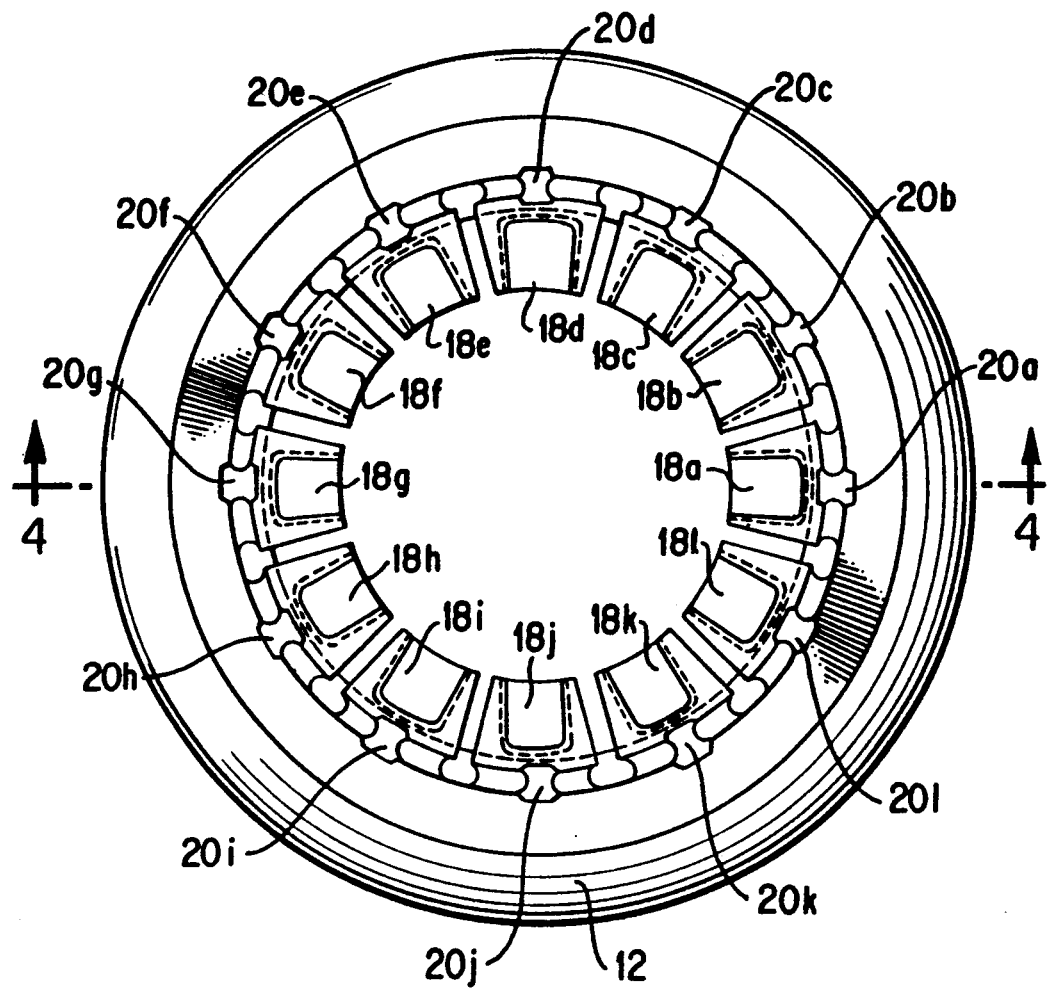
FIG. 3 is a top view of the ring portion of the sensor shown in FIG. 1.

The ring 12 is carried by the lower gauge support member 32 on the opposite side of the moving sheet 14. As previously mentioned, the two support members are vertically aligned to maintain the lowest point of rotating wheel 16 substantially centered in the open region defined by the ring 12. The upper surface of the ring 12 provides a support surface for the moving sheet 14. As seen in FIG. 3, twelve independently movable segments 18a-18l are uniformly distributed around the inner periphery of the ring 12.

Figure 4:
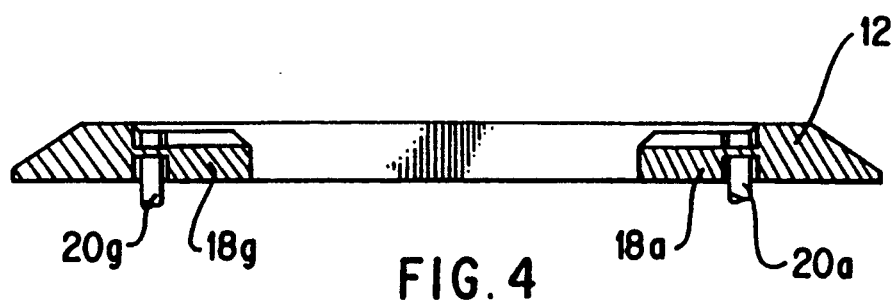
FIG. 4 is a cross sectional view of the ring portion taken along line 4—4 in FIG. 3.

When the sheet 14 is deflected, best seen in FIG. 2, it exerts a force against each segment 18a-18l. This force is detected by load cells 20a-20l, seen in FIGS. 2 and 4. In the illustrated embodiment cantilever load cells are shown. However, different types of load cells may be desirable in different applications of the present sensor.

In the illustrated embodiment, there are an even number of segments 18a-18l distributed about the ring such that each segment has a corresponding segment directly opposite on the other side of the ring. For example, segment 18a is directly opposite segment 18g. As a result, each opposing pair of segments defines a different line passing through the center of the ring. In the illustrated embodiment, there are six pair of segments defining six different lines. Each line passes through the center of the ring and extends in a different direction. In this manner, the load cells associated with any opposing pair of segments detect the force exerted by the deflected sheet in the direction of the line defined by the segments. As a result, a sensor in accordance with the present invention can detect directional variations in the force exerted by the deflected sheet.

Of course, the number of directions in which the sensor can detect the force exerted by the deflected sheet depends on the number of segments provided on the ring. Further, because the force detected by each load cell is actually the force exerted by the deflected sheet over the entire arc defined by the associated segment, the resolution of the sensor depends on the size of each segment. The illustrated embodiment uses twelve segments each of which covers an arc of approximately thirty degrees. This has been found suitable for the detection of fiber orientation in paper. However, in other applications it may be desirable to employ a different number of segments, segments of a different size, or both.

The force exerted by the deflected sheet against any particular segment is the result of three additive factors. The first factor is the stress in the sheet caused by the strain due to local distortion by the wheel when it deflects the sheet into the open region of the ring. This is the extensional stiffness of the sheet. The second factor is the tension in the sheet. It has been found that for all practical purposes the only tension in the sheet is that generated in the machine direction by the manufacturing machinery. The third additive factor is the bending stiffness of the sheet. Mathematically, the combined outputs of the load sensors corresponding to an opposing pair of segments can be expressed as follows:

$$\text{OUTPUT}_{ag} = (A_{ag})(E_{ag})(t)(f_1(z^n)) + (B_{ag})(T_{ag})(z) + (C_{ag})(\beta_{ag})(z) \quad (1)$$

Where:

$\text{OUTPUT}_{ag}$ = the sum of the force of the deflected sheet against two opposing segments, for example segments 18a and 18g as indicated by the subscripts.

$E_{ag}$ = Young's modulus of the sheet in the direction of the segments.

$t$ = the caliper of the sheet.

$z$ = the distance which the sheet is deflected.

$f_1$ = a function of z raised to a power greater than one relating the extensional stiffness of the sheet (i.e., (E)(t)) to the stress in the sheet caused by sheet strain as the wheel pushes the sheet into the opening defined by the ring.

$T_{ag}$ = the tension in the sheet along the direction of the segments. Although the only tension is in the machine direction, each segment subtends an arc and will have an effective width in the machine direction. Hence, each segment will be somewhat affected by the machine directed tension. The effective width of each segment can be empirically determined if desired.

$\beta_{ag}$ = the bending resistance of the sheet in the direction of the segments.

$A_{ag}$, $B_{ag}$, and $C_{ag}$ = empirically determined proportionality constants.

The equations above are subject to a variety of mathematical solutions with many of the variables being determined with existing sensors or gauges. For example, commonly assigned and copending U.S. patent application Ser. No. 07/247,177, now U.S. Pat. No. 5,029,469, issued Jul. 9, 1991, which is incorporated herein by reference, discusses the solution of similar equations and describes sensors for determining sheet tension and extensional stiffness.

Figure 5:
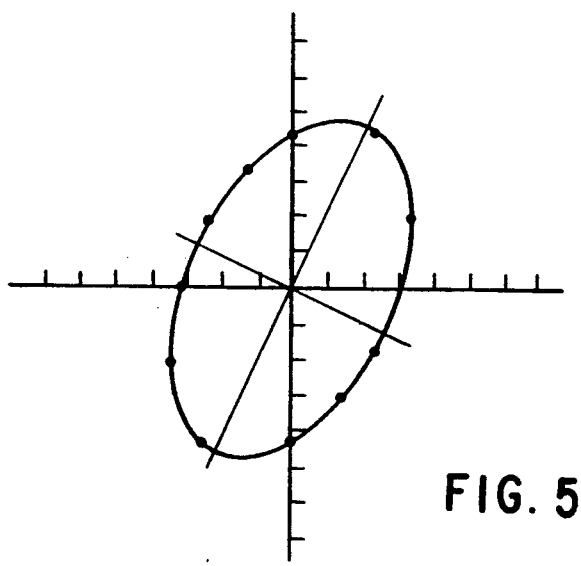
FIG. 5 is a polar plot of the extensional stiffness as determined by the sensor.

However, in the preferred embodiment of the present sensor solution of the equations to find the fiber orientation of the sheet is greatly simplified. This is because it has been found that fiber orientation may be directly related to extensional stiffness, i.e., the first term of equation (1). In particular, as illustrated in FIG. 5, a polar graph of the extensional stiffness of the moving sheet forms a shape which may be approximated as an ellipse. The angle between the major axis of the ellipse and the machine direction corresponds with the fiber orientation angle. Moreover, the ratio of the major axis of the ellipse to the minor axis of the ellipse is an indication of the degree of anisotropism of the sheet. As a result, by determining the extensional stiffness of the sheet in the direction of each pair of opposing segments, the present sensor can be used to determine the fiber orientation of the sheet.

The first term of equation (1) is a function of z raised to a power greater than one. However, the second and third terms, tension and bending stiffness, respectively, are linear functions of z. Therefore, if both sides of equation (1) are divided by z the second and third terms of equation become independent of z, as shown in equation (2).

$$\text{OUTPUT}/z = (A)(E)(t)(f(z^{n-1})) + (B)(T) + (C)(\beta) \quad (2)$$

Furthermore two equations, (3) and (4), can be established by making two measurements with two different z values.

$$\text{OUTPUT}_1/z_1 = (A)(E)(t)(f(z_1^{n-1})) + (B)(T) + (C)(\beta) \quad (3)$$

$$\text{OUTPUT}_2/z_2 = (A)(E)(t)(f(z_2^{n-1})) + (B)(T) + (C)(\beta) \quad (4)$$

Subtracting equation (4) from equation (3) yields equation (5) and eliminates the tension and bending stiffness terms completely.

$$\text{OUTPUT}_1/z_1 - \text{OUTPUT}_2/z_2 = (A)(E)(t)(f(z_1^{n-1}) - f(z_2^{n-1})) \quad (5)$$

The right hand side of equation (5) is proportional to the extensional stiffness. It is unnecessary to evaluate the proportionality constant because it will not affect the orientation or the ratio of the major axis to the minor axis of the ellipse formed by the polar plot of the extensional stiffness. For the same reason, it is not necessary to evaluate the caliper of the sheet, t. However, the caliper can be easily and routinely determined using a number of readily available caliper gauges.

To implement the equations outlined above, the sensor must make two different measurements. One at a first deflection distance, or z value, and another at a second deflection distance, different from the first. In the preferred embodiment, this is accomplished by adjusting the air cylinder 40 to cause the wheel to deflect the sheet a first distance into the open region defined by the ring; scanning the sensor across the width of the sheet and determining the output of each load cell at predetermined slices during the scan; storing the outputs of each load cell at each slice; adjusting the air cylinder to cause the wheel to deflect the sheet a second distance into the ring; scanning the sensor back across the sheet and determining the output of each load cell at each slice; and using the stored first output, the first deflection distance, the second output, and the second deflection distance to solve equation (5) for each opposing pair of segments at each slice across the sheet.

Of course, using this method, because the sheet is moving, the two measurements at different deflections do not correspond to exactly the same part of the moving sheet. However, it has been found that under normal operating conditions, fiber orientation typically changes very slowly in the machine direction. Therefore any error introduced by taking the two different measurement at different locations along the machine direction of the sheet is negligible.

The distance which the sheet is deflected at any given adjustment may be determined by means of a displacement sensor 42. The displacement sensor can be any one of a variety of known sensors, such as an eddy current device, which uses magnetic fields to determine the position of the wheel 16 and hence the deflection distance of the sheet 14. The actual deflection distance is not critical to the invention and will vary depending on the geometry of the sensor. However, in the illustrated embodiment having a wheel with a diameter of about 5 inches and a ring defining an open region with a diameter of about 3.5 inches, deflections of about 0.14 inches and about 0.08 inches have proved satisfactory.

In the preferred embodiment, control of the air cylinder 40, and hence the displacement of the sheet, as well as the control of the scanning station to implement the steps described above can be facilitated by an appropriately programmed computer. The computer can also be programmed to monitor the outputs from the load cells, solve the equations described above, and determine the fiber orientation of the sheet.

This detailed description is set forth only for purposes of illustrating examples of the present invention and should not be considered to limit the scope thereon in any way. Although the described embodiment has the wheel positioned above the sheet and the ring positioned below the sheet, it is equally possible, and in some circumstances may be desirable to position the ring above the sheet and the wheel below the sheet. Clearly numerous other additions, substitutions, and other modifications can be made to the invention without departing from the scope of the invention. which is defined in the appended claims and equivalents thereof.

What is claimed is:

1. A sensor for determining directional variations in a physical characteristic of a moving sheet of fibrous material, said characteristic being related to the orientation of the fibers within said material, said sensor comprising:
   a non-rotatable support for supporting the moving sheet, said support defining an opening;
   a deflector for deflecting the sheet into the opening;
   a plurality of detectors associated with the support, said detectors arranged to detect a physical parameter related to the force exerted on the support by the deflected sheet in at least three different directions and produce a plurality of signals, each signal indicative of the detected physical parameter in one of said directions; and
   electronic circuits, operatively coupled to the detectors, to receive the signals, wherein the circuits are adapted to determine information relating to directional variations in said physical characteristic of the sheet based upon the signals and to determine said fiber orientation based on said information.

2. The sensor of claim 1 wherein the support includes at least three pairs of sheet supporting segments movable independently in the direction of sheet deflection disposed about the opening with one member of each pair being situated on the opposite side of the opening from the other member, each pair of supporting segments defining one of said directions.

3. The sensor of claim 2 wherein the deflector includes a rotatable wheel disposable within the opening.

4. The sensor of claim 3 further comprising means for measuring the distance which the sheet is deflected.

5. The sensor of claim 4 further comprising means for controlling the distance which the sheet is deflected.

6. The sensor of claim 5 wherein there are at least six pair of supporting segments.

7. The sensor of claim 1 wherein said physical characteristic is extensional stiffness.

8. An on-line fiber orientation sensor for determining the orientation of fibers in a moving fibrous sheet, comprising:
   a support for supporting the moving sheet, said support defining an opening;
   a deflector for deflecting the sheet into the opening;
   three pairs of supporting segments carried by the support, each supporting segment being independently movable in the direction of sheet deflection, the supporting segments distributed about the inner periphery of the opening with one member of each pair positioned directly opposite the other member of the pair to define three different lines, each line passing through the deflector;
   a detector associated with each of the supporting segments for detecting a physical parameter related to the force exerted by the deflected sheet in a direction along the line defined by the associated pair of supporting segments and producing a signal indicative of the physical parameter; and
   circuit means, operatively coupled to the detectors, for receiving the signals from the detectors and determining information relating to the orientation of fibers within the moving sheet.

9. The sensor of claim 8 wherein the support and the deflector are adapted to be positioned on opposite sides of the moving sheet.

10. The sensor of claim 9 wherein there are six pair of supporting segments.

11. The sensor of claim 10 wherein the deflector is adapted to deflect the sheet a predetermined distance into the opening.

12. A method of measuring the directional variations in a physical characteristic in a moving sheet of fibrous material, said moving sheet having a direction of travel, said characteristic being related to the orientation of the fibers within said material, said method comprising the steps of:
   supporting one side of the moving sheet at a plurality of regions by means of a non-rotatable support, said plurality of regions defining an unsupported region therebetween;
   deflecting the sheet into the unsupported region;
   detecting a physical parameter related to the force of the sheet against the plurality of regions in at least three different directions, said at least three different directions being substantially fixed relative to the direction of travel of the moving sheet;
   determining the directional variation of the physical characteristic based upon the detected physical parameter in the at least three directions; and
   determining the fiber orientation angle based upon the directional variation of the physical characteristic.

13. The method of claim 12 further comprising the step of determining the degree of anisotropism of the fibers in the sheet based upon the directional variation of the physical characteristic.

14. The method of claim 12 wherein the physical characteristic is extensional stiffness.

15. A sensor for determining directional variations in a physical characteristic of a moving sheet of fibrous material, said characteristic being related to the orientation of the fibers within said material, said sensor comprising:
   a support for supporting the moving sheet, said support defining an opening and including at least three pairs of sheet supporting segments movable independently in the direction of sheet deflection disposed about the opening with one member of each pair being situated on the opposite side of the opening from the other member, each pair of supporting segments defining one of said directions;

a deflector for deflecting the sheet into the opening;

a plurality of detectors associated with the support, said detectors arranged to detect a physical parameter related to the force exerted on the support by the deflected sheet in at least three different directions and produce a plurality of signals, each signal indicative of the detected physical parameter in one of said directions; and electronic circuits, operatively coupled to the detectors, to receive the signals, wherein the circuits are adapted to determine information relating to directional variations in said physical characteristic of the sheet based upon the signals and to determine said fiber orientation based on said information.

16. The sensor of claim 15 wherein the deflector includes a rotatable wheel disposable within the opening.

17. The sensor of claim 16 further comprising means for measuring the distance which the sheet is deflected.

18. The sensor of claim 17 further comprising means for controlling the distance which the sheet is deflected.

19. The sensor of claim 18 wherein there are at least six pair of supporting segments.

* * * * *